US00PP18911P2

(12) United States Plant Patent
Vorsa

(10) Patent No.: US PP18,911 P2
(45) Date of Patent: Jun. 10, 2008

(54) CRANBERRY VARIETY NAMED 'NJS98-35'

(50) Latin Name: *Vaccinium macrocarpon Ait.*
Varietal Denomination: NJS98-35

(75) Inventor: Nicholi Vorsa, Atco, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 30 days.

(21) Appl. No.: 11/657,846

(22) Filed: Jan. 24, 2007

(51) Int. Cl.
*A01H 5/00* (2006.01)

(52) U.S. Cl. ..... Plt./156

(58) Field of Classification Search ..... Plt./156
See application file for complete search history.

*Primary Examiner*—Annette H Para
(74) *Attorney, Agent, or Firm*—Klarquist Sparkman, LLP

(57) ABSTRACT

A new cranberry variety distinguished by significantly higher yields, higher anthocyanin content (red pigment), lower titratable acidity, and larger fruit size. In addition, high TAcy values in September provide for an earlier harvest window for processed fruit, especially relative to 'Stevens' (unpatented), a primary commercial variety.

2 Drawing Sheets

STATEMENT REGARDING FEDERALLY SPONSORED RESEARCH OR DEVELOPMENT

This invention was made in part with United States Government support awarded by the U.S. Department of Agriculture, Cooperative State Research, Education and Extension Service, under grant SRG 88-34155-3491. Therefore, the Government may have certain rights in this invention.

Latin name of the genus and species of the plant claimed: *Vaccinium macrocarpon* Ait.

Variety denomination: 'NJS98-35'.

BACKGROUND OF THE INVENTION

The present invention relates to a new and distinct American cranberry variety having a combination of traits, including significantly higher yields and higher anthocyanin (red pigment) content, as compared to currently cultivated commercial varieties. The new variety, 'NJS98-35', resulted from crossing the variety 'Franklin' (unpatented) as the seed parent and the variety 'Ben Lear' (unpatented) as the pollen parent. The parent varieties are genetically distinct from the majority of cranberries in production today. As such, 'NJS98-35' offers growers an opportunity to increase the genetic diversity of their cranberry beds while increasing yields. The plant was originally selected from over 1,500 seedlings growing in test plots in Chatsworth, N.J. and Portage County, Wis.

The American cranberry (*Vaccinium macrocarpon* Ait.) is a temperate, woody perennial plant species native to North America. The United States is the largest producer, with Wisconsin and Massachusetts representing the majority of cranberry acreage and production, followed by New Jersey, Oregon and Washington. The cranberry industry relies on relatively few cranberry varieties, representing a narrow genetic base. These varieties are clonally-propagated and include selections from native populations and first generation hybrids. Significant acreage is still devoted to varieties that were selected from native cranberry populations from as far back as 1850, including 'Ben Lear' (unpatented), 'Early Black' (unpatented), 'Howes' (unpatented), 'Lemunyon' (unpatented), 'McFarlin' (unpatented), and 'Searles' (unpatented). The hybrid varieties were developed from one cycle of breeding and selection that was conducted by the United States Department of Agriculture, in cooperation with state Agricultural Experiment Stations in the 1940's. This breeding program released a series of unpatented varieties in the 1950's including the most widely grown cultivar 'Stevens' (unpatented), which was selected from test plots in Pemberton, N.J.

Varieties having high anthocyanin production along with consistently high productivity have become essential for commercial success in cranberry production. Fruit crop productivity is a function of inherent differences among varieties for traits such as stolon vigor, upright density, inflorescence bud production, fruit set and fruit size. Varieties with high stolon vigor will establish more rapidly and reduce the number of years required to achieve maximal production. However, after bed establishment, varieties must transition to optimal sexual reproduction mode, and optimal upright density, to achieve high crop production. Cranberry inflorescence bud primordia are set on uprights during the completion of the fruit development period and overwinter in a dormant state, before resuming growth the subsequent spring. Thus, the crop load of a given year, may impact the subsequent year's crop, contributing to the pronounced biennial bearing habit common to many varieties. Productivity is also subject to environmental effects, e.g., heat and light intensity stresses, cold (frost) stress, water stress (drought and excess), disease, insects, and certain pesticides.

TAcy, fruit anthocyanin content, is currently a fruit quality component of processed cranberry, having a minimum acceptable value, as well as premiums for fruit with higher TAcy values. TAcy is measured in terms of mg of anthocyanin per 100 g fruit using a standard spectrophotometric (520 nm) method. Earlier ripening varieties, which typically have higher TAcy, allow for earlier harvesting of a crop. Anthocyanins are largely located in the fruit epidermis, which results in larger fruit generally having lower TAcy. The Rutgers University cranberry breeding program quantitatively measured TAcy along with mean fruit size, and selected progeny with large fruit size and high TAcy levels.

New Jersey uniquely offers an ideal environment for cranberry breeding because of the climate, soils and water. Of all the cranberry production areas in North America, New Jersey conditions subject the cranberry to the highest disease pressure and heat stress. The plant must tolerate high heat stress and vegetative diseases during the growing season. The fruit is subject to over 15 pathogens known to incite cranberry fruit rot in New Jersey, as well as heat scald and physiological breakdown. Thus, selection under New Jersey conditions offers an opportunity to identify varieties with higher resistance to disease, scald, and heat stress.

The Rutgers University cranberry breeding program, in Chatsworth, N.J., was initiated in 1985 to take advantage of this unique selection pressure. The program's methods were designed to duplicate, as much as possible, the environment of a commercial bed. Thus, breeding plots of 1.5×1.5 m were established with multiple plants and allowed to fill in to form a dense canopy. Two to four years after planting, yields of a given plot was evaluated over a four year minimum to provide for biennial bearing assessment. Parental selection was based on fields phenotypic performance, and parental cross combinations were based on the objectives of enhancing traits and/or combining the most desirable traits from both parents into one genotype, i.e., variety. Traits being evaluated in Rutgers University's cranberry breeding program include yield, fruit rot susceptibility/resistance, scald, stolon and upright vigor, total anthocyanin content (TAcy), soluble solids (Brix), and titratable acidity.

The new variety described herein, 'NJS98-35', resulted from crossing the variety 'Franklin' (unpatented) as the seed parent, with the variety 'Ben Lear' (unpatented) as the pollen parent. The plant was originally selected from a group of plants sexually derived from the same parents as the new variety and that were grown in a field trial of over 1,500 seedlings representing 15 cross combinations growing in test plots planted in 1993 in Chatsworth, N.J. Clones of these seedlings were also planted at a second location, Portage County, Wis. In 1998, 55 plants (clones) were selected from this trial, and were planted in a replicated trial with 3×10 m plots in City Point, Wis. Twenty-six of these selections were also planted in 3×3 m plots in Chatsworth, N.J. for additional evaluations. 'NJS98-35' consistently performed significantly better than standard varieties in these trails. 'NJS98-35' has also been planted in a larger evaluation bed (0.6 acre) in 2005 in Browns Mills, N.J.

'NJS98-35' is a new cranberry variety selected under New Jersey's stressful conditions, which offers the potential for high yields, early ripening and higher TAcy content.

BRIEF SUMMARY OF THE INVENTION

The 'NJS98-35' variety is distinguished from other cranberry varieties due to the following unique combination of characteristics: significantly higher yield, higher total anthocyanins, lower titratable acidity and larger fruit size than other commercial varieties, such as 'Stevens' (unpatented) and 'Ben Lear' (unpatented).

'NJS98-35' has been asexually reproduced by cuttings at the Marucci Center for Blueberry and Cranberry Research and Extension Center, Chatsworth, N.J. since 1992. Over that period, no evidence of off-types of 'NJS98-35' has been observed or reported to us. Thus, it is concluded that 'NJS98-35' is stable and reproduces true to type in successive generations of asexual reproduction.

The following detailed description concerns the variety 'NJS98-35'. The original plant and vegetative propagules have been observed growing in cultivated areas in Chatsworth and Browns Mill, N.J., and Portage County and City Point, Wis. Certain characteristics of this variety, such as growth and color, may change with changing environmental conditions (such as light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart.

Figure 1:
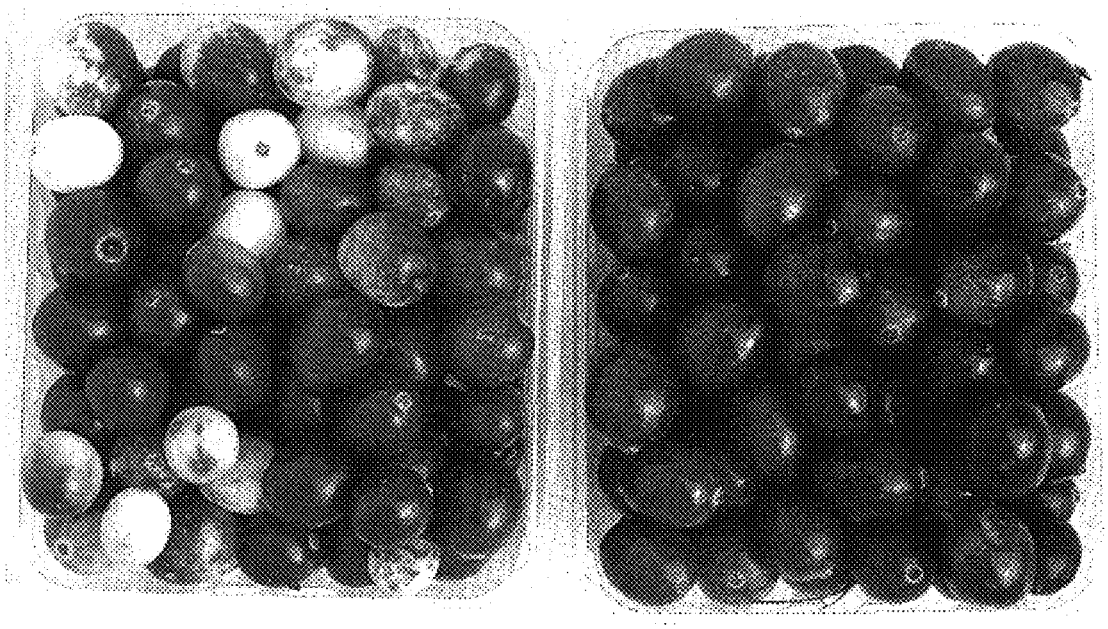
FIG. 1 compares 'NJS98-35' fruit (on the right) with 'Stevens' (unpatented) fruit harvested Oct. 3, 2006 from the same cranberry bed in City Point, Wis.
Figure 2:
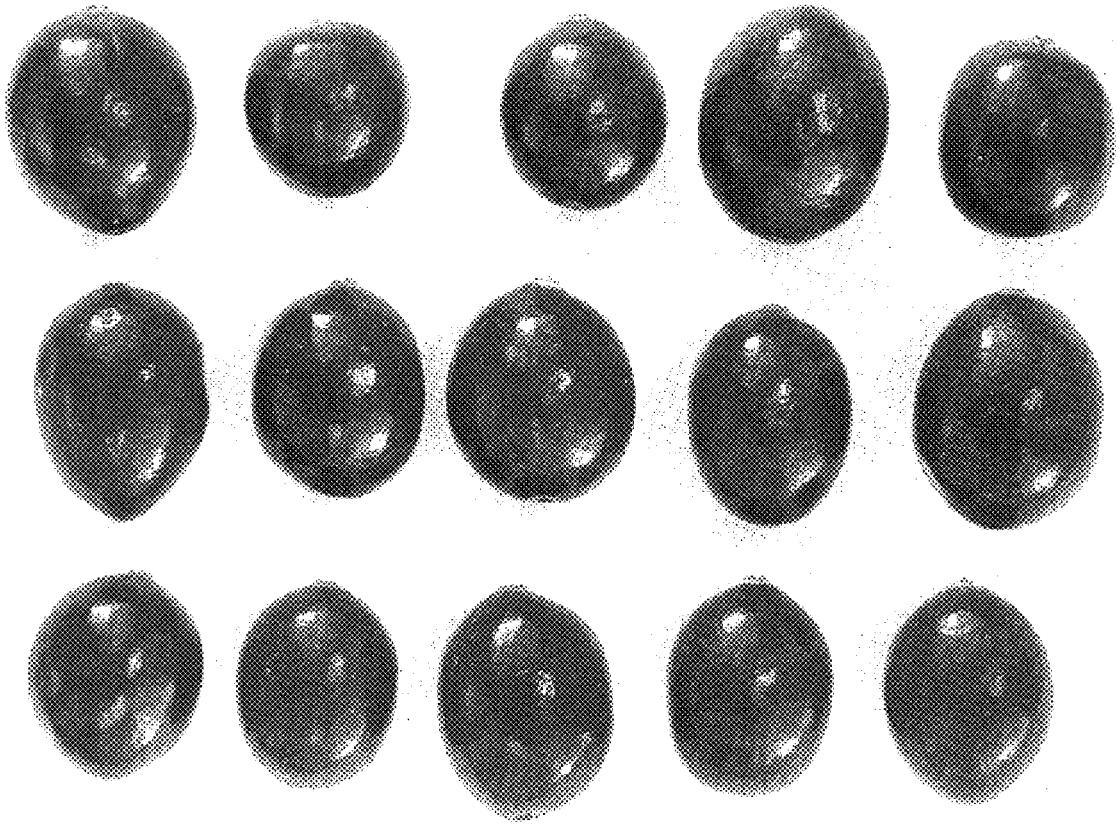
FIG. 2 shows the size, shape and color of 'NJS98-35' fruit harvested Oct. 3, 2006 from City Point, Wis.

The colors of an illustration of this type may vary with lighting and other conditions under which conditions and, therefore, color characteristics of this new variety should be determined with reference to the observations described herein, rather than from these illustrations alone.

DETAILED BOTANICAL DESCRIPTION

The following detailed description of the 'NJS98-35' variety is based on observations of plants growing in the field on Chatsworth, N.J. and City Point, Wis. The characteristics of the variety were compared to 'Stevens' (unpatented) and 'Ben Lear' (unpatented), two of the most widely used cranberry varieties. The observed propagules were 3–8 years of age.

Scientific name: *Vaccinium macrocarpon* Ait.

Parentage:

*Seed parent.*—The variety 'Franklin' (derived from an 'Early Black'×'Howes' cross) (unpatented).

*Pollen parent.*—The variety 'Ben Lear' (selected from the wild in 1900 in Berlin, Wis.) (unpatented).

Plant:

*Vigor.*—General observations of 'NJS98-35' plantings indicate average plant vigor. The amount of growth generated from 1 cutting planted in a 3" pot in May 2006 (3 pots per variety) was measured after 4 months; 'NJS98-35' had 94 cm of top growth, 'Stevens' (unpatented) had 88 cm, and 'Ben Lear' (unpatented) had 104 cm.

*Growth habit.*—Trailing shrub with very slender stems. 'NJS98-35' is more shrub-like than 'Stevens' (unpatented), especially in new plantings. In a 4 month old planting, 'NJS98-35' had longer uprights (10.5 cm vs. 9.2 cm) and shorter runners (47.8 cm vs. 76.3 cm) than 'Stevens' (unpatented).

*Runner length.*—Average runner length was 47.8 cm in a 4 month-old field planting.

*Upright length.*—Average upright length ranged from 10.5 cm in a 4 month-old field planting to 9.6 cm in a 4 yr-old planting.

*Stem diameter.*—Average stem diameter was 1.3 mm at base of current year's growth.

*Internodes.*—Average internode length was 8.1 mm on a 1-year old runner.

*Productivity.*—In established test plots in Chatsworth, N.J., 'NJS98-35' produced an average of 348 g of berries/sq. ft. (38 g/dm$^2$) in comparison to 'Stevens' (unpatented) yield of 280 g/sq. ft. (30 g/dm$^2$) (4-year averages, see Table 1). In established plots in City Point, Wis., 'NJS98-35' produced an average of 377 g of berries/sq. ft. (41 g/dm$^2$) in comparison to 'Stevens' (unpatented), 261 g/sq. ft. (28 d/cm$^2$), and 'Ben Lear' (unpatented), 322 g/sq. ft. ) (35 g/dm$^2$ (5-year averages, see Table 2).

*Hardiness.*—Zones 4–7 (from USDA Misc. Publ. 814).

*Disease and Resistance.*—No disease resistance data available for foliar or root pathogens.

*Leaves.*—The length, width and other measurements were obtained from observations of 20 typical fully developed leaves on Nov. 16, 2004 from a 6-yr. old field plot. Color was determined on actively growing plants.

*Texture.*—Coriaceous (leathery).

*Length.*—About 9.1 mm to about 11.6 mm, averaging 10.2 mm.

*Width.*—About 3.7 mm to about 5.1 mm, averaging 4.3 mm.

*Shape.*—Elliptic (2.4:1 ratio).

*Apex shape.*—Rounded.

*Base shape.*—Rounded, nearly sessile.

*Margin.*—Entire, slightly revolute.

*Leaf color.*—Upper leaf surface color ranges from bright green (RHS 143C) in new growth, to deep green in mature leaves (RHS 139A to 137C).

*Pubescence.*—A small number of non-glandular trichomes found at tip and margins of leaf.

Flowers:

*Size and shape.*—Slender, nodding flowers on erect pedicels and in clusters of 3–5 flowers, corolla long-conic in bud, petals divided nearly to the base when open; typical open flower measuring about 10 mm across.

*Color.*—Unopened bud: deep pink (RHS 68C). Opened flower: pale pink (RHS 69A & B).

*Petals.*—4 petals per flower; narrow and revolute in shape.

*Bloom season.*—Bloom typically begins in early June and continues until early July, depending on the season. Peak blooms for 'NJS98-35' is 1–2 days earlier than 'Stevens' (unpatented). On Jun. 22, 2005 in Chatsworth, N.J., 'NJS98-35' had reached 77% bloom while 'Stevens' (unpatented) was 53% in bloom; on Jun. 22, 2006 in City Point, Wis., 'NJS98-35' was 72% in bloom while 'Stevens' (unpatented) was 59% in bloom.

*Mean number of flowers per upright.*—4.6.

Fruit: Observations are from 30 typical fruit harvested from test plots in Chatsworth, N.J. and 30 fruit from City Point, Wis. on Oct. 10, 2004.

*Shape.*—Elliptic, with rounded to slightly pointed stem end, and slightly protruding calyx.

*Size.*—The fruit size of 'NJS98-35' is larger than many standard varieties. In NJ, average fruit size was 2.2 nm long by 1.7 cm wide, compared to 'Stevens' (unpatented), 2.1 cm long by 1.6 cm wide. In Wis., 'NJS98-35' fruit was 2.0 cm long by 1.6 cm wide, compared to 'Stevens' (unpatented), 1.9 cm long by 1.6 cm wide. Another measure of fruit size in the cranberry industry is the 'cup count', the number of fruit that fits in a standardized cup. 'NJS98-35' cup count is 44, compared to 'Stevens' (unpatented) cup count of 53.

*Skin.*—Shiny with little to no bloom, except waxy bloom around calyx.

*Color.*—Ranged from red (RHS 46A) for the lighter berries, dark red (RHS 185A) for medium berries, to dark pink (RHS 186A) for the darkest (harvested Oct. 1, 2006).

*Stem pit.*—Medium in width and slightly intended (2.7 mm in diameter for 'NJS98-35' and 2.9 mm for 'Stevens' (unpatented)).

*Average weight.*—In NJ, 2.3 g; in WI, 2.2 g. Fruit collected yearly from 1 ft$^2$ samples in test plots had an average weight of 2.3 g in NJ and 2.1 in WI, larger than 'Stevens' (unpatented) in both locations (Tables 1 & 2).

*Number of seeds.*—An average of 22 seeds per fruit, similar to 'Stevens' (unpatented), and more than 'Ben Lear' (unpatented).

*Fruit chemistry.*—100 g samples of the fruit were harvested each year from test plots in Chatsworth, N.J. and City Point, Wis. and evaluated for fruit chemistry. 'NJS98-35' fruit, harvested in Wisconsin in October, consistently had twice the TAcy values as 'Stevens' (unpatented) (Table 3). In New Jersey, 'NJS98-35' TAcy values were four times greater than 'Stevens' (unpatented) in September, and 60% greater than 'Stevens' (unpatented) in October (Table 4). A TAcy of 31 mg/100 g fruit on Sept 10 provides for an earlier harvest for processed fruit. 'NJS98-35' had titratable acidity values lower than 'Stevens' (unpatented) in both Wisconsin (2.3% vs. 2.6%) and New Jersey trials (2.1% vs. 2.4%). Brix and proanthocyanidin values were comparable to 'Stevens' (unpatented).

*Fruit production.*—First picking date in New Jersey was September 10. Average production was 348 g of berries/ft$^2$ (38 g/dm$^2$) in NJ plots, approximately equivalent to 335 barrels/acre; and 377 g of berries/ft$^2$ (41 g/dm$^2$, 363 bbl/A) in WI test plots (Tables 1 & 2).

*Usage.*—Processing and fresh fruit.

*Disease resistance.*—In the Wisconsin trial, 'NJS98-35' had 9% fruit rot (mean of October 2001, 2002, 2005 and 2006), the same as 'Ben Lear' (unpatented) and slightly more than 'Stevens' (unpatented). In New Jersey where disease pressure is greater, 'NJS98-35' had an average of 24% fruit rot (2001–2004).

TABLE 1

Yield and fruit weight comparisons from a research trial established May 1999, in Chatsworth, NJ.

| | Total yield, g/ft$^2$ | | | | |
|---|---|---|---|---|---|
| Cultivar | 2001 Mean | 2002 25 Oct. | 2003 mean | 2004 mean | 01-04 Mean |
| 'NJS98-35' | 357 | 243 | 330 | 463 | 348 |
| 'Stevens' | 210 | 227 | 336 | 348 | 280 |

TABLE 1-continued

Yield and fruit weight comparisons from a research trial established May 1999, in Chatsworth, NJ.

| | Fruit wt., g/berry | | | | |
|---|---|---|---|---|---|
| Cultivar | 2001 Mean | 2002 25 Oct. | 2003 mean | 2004 mean | 01-04 mean |
| 'NJS98-35' | 2.2 | 2.5 | 2.4 | 2.2 | 2.3 |
| 'Stevens' | 2.2 | 2.2 | 2.3 | 1.8 | 2.1 |

TABLE 2

Yield and fruit weight comparisons from a replicated trial established May 1999, in City Point, WI.

| | Total yield, g/ft$^2$ | | | | | |
|---|---|---|---|---|---|---|
| Cultivar | 4 Oct. 2002 | 9 Oct. 2003 | 9 Oct. 2004 | Mean 2005* | 29 Sep. 2005 | 02-06 Mean |
| 'NJS98-35' | 222 | 413 | 427 | 434 | 388 | 377 |
| 'Ben Lear' | 189 | 273 | 338 | 356 | 455 | 322 |
| 'Stevens' | 106 | 197 | 374 | 229 | 400 | 261 |
| | Fruit wt., g/berry | | | | | |
| Cultivar | 4 Oct. 2002 | 9 Oct. 2003 | 9 Oct. 2004 | Mean 2005* | 29 Sep. 2005 | 02-06 Mean |
| 'NJS98-35' | 2.3 | 2.1 | 2.0 | 2.0 | 2.1 | 2.1 |
| 'Ben Lear' | 2.0 | 1.6 | 1.5 | 1.6 | 1.6 | 1.6 |
| 'Stevens' | 1.8 | 1.8 | 1.7 | 1.7 | 1.8 | 1.8 |

*2005 mean of 3 dates, 19 Sep., 3 Oct., 15 Oct..

TABLE 3

Fruit color comparisons of 'NJS98-35' with 'Ben Lear' and 'Stevens', in 2001-2006 in City Point, WI

| | TAcy, mg/100 g frt | | | | | | |
|---|---|---|---|---|---|---|---|
| Cultivar | 19 Oct. 2001 | 4 Oct. 2002 | 9 Oct. 2003 | 9 Oct. 2004 | 3 Oct. 2005 | 29 Sep. 2006 | 01-06 Mean |
| 'NJS98-35' | 52 | 53 | 60 | 65 | 38 | 47 | 52 |
| 'Ben Lear' | 60 | 40 | 46 | 56 | 32 | 50 | 47 |
| 'Stevens' | 26 | 26 | 27 | 35 | 12 | 28 | 26 |

TABLE 4

Fruit color comparisons of 'NJS98-35' and 'Stevens', in 2001-2004 in Chatsworth, NJ.

| | TAcy, mg/100 g fruit | | | | | | | |
|---|---|---|---|---|---|---|---|---|
| Cultivar | 10 Sep. 2001 | 15 Oct. 2001 | 25 Oct. 2002 | 15 Sep. 2003 | 6 Oct. 2003 | 24 Sep. 2004 | 11 Oct. 2004 | Oct. mean 2001-04 |
| 'NJS98-35' | 31 | 57 | 62 | 18 | 47 | 39 | 59 | 54 |
| 'Stevens' | 5 | 37 | 44 | 4 | 27 | 11 | 24 | 34 |

I claim:

1. A new and distinct variety of cranberry plant, substantially as herein shown and described.

* * * * *